US00PP31963P2

(12) United States Plant Patent
Cannon

(10) Patent No.: US PP31,963 P2
(45) Date of Patent: Jul. 14, 2020

(54) SOUTHERN RED CEDAR TREE NAMED 'CAN-SRC1'

(50) Latin Name: ***Juniperus virginiana* var. *silicicola***
Varietal Denomination: CAN-SRC1

(71) Applicants: Taylor-Cade Trees Inc., Center Hill, FL (US); Cannon Trees Inc., Brooksville, FL (US)

(72) Inventor: Adam Cannon, Brooksville, FL (US)

(73) Assignees: Taylor-Cade Trees Inc., Center Hill, FL (US); Cannon Trees Inc., Brooksville, FL (US)

( * ) Notice: Subject to any disclaimer, the term of this patent is extended or adjusted under 35 U.S.C. 154(b) by 0 days.

(21) Appl. No.: 16/501,511

(22) Filed: Apr. 23, 2019

(51) Int. Cl.
*A01H 7/00* (2006.01)

(52) U.S. Cl.
USPC ..... Plt./214

(58) Field of Classification Search
USPC ..... Plt./214
CPC ..... A01H 7/00; A01H 5/08
See application file for complete search history.

(56) References Cited

PUBLICATIONS

University of Wisconsin Green Bay Cofrin Center for Biodiversity Trees of Wisconsin, retrieved on Dec. 4, 2019, retrieved from the Internet at https://www.uwgb.edu/biodiversity/herbarium/gymnosperms/junvir01.htm, 2 pp. (Year: 2019).*

* cited by examiner

*Primary Examiner* — June Hwu
(74) *Attorney, Agent, or Firm* — Panitch Schwarze Belisario & Nadel LLP

(57) ABSTRACT

A new and distinct variety of southern red cedar tree, herein referred to by its cultivar name, 'CAN-SRC1', is provided which forms fibrous, highly branching, high density roots. Alternating random branch pattern is displayed. Attractive, acicular shaped needles are formed which display an alternate arrangement. Juniper-like fragrance is exhibited. Resistance to fungus and spider mites is good. The new variety is well suited for providing attractive ornamentation in the landscape.

5 Drawing Sheets

Botanical/commercial classification:
Latin name—*Juniperus virginiana* var. *silicicola*.
Common name—Southern red cedar.
Varietal denomination: 'CAN-SRC1'.
Trademark name: FUZZY WUZZY.

SUMMARY OF THE INVENTION

A chance seedling of the new variety of the southern red cedar tree was discovered in a cultivated area, namely the inventor's red cedar tree fields. Neither the female parent (i.e., the seed parent) nor the male parent (i.e., the pollen parent) of the new variety is known.

The parentage of the new variety can be summarized as follows:

'Unknown' x 'Unknown'

It was found that the new variety of southern red cedar tree of the present invention possesses the following combination of characteristics:

(a) forms attractive, acicular shaped, alternate arranged needles
(b) provides Juniper-like fragrance,
(c) exhibits fibrous, highly branching, high density root habit, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from related similar varieties. For example, the 'Robin Blue' variety (non-patented) displays a less upright habit compared to the new variety. In addition the new variety exhibits a finer needle compared to the 'Robin Blue' variety.

The new variety has been found to undergo asexual propagation in Eustis, Fla. by vegetative cuttings. Asexual propagation by vegetative cutting in Eustis, Fla. has shown that the characteristics of the new variety are stable and are strictly transmissible by such asexual propagation from one generation to another. Accordingly, the new variety undergoes asexual propagation in a true-to-type manner.

The new variety has been named 'CAN-SRC1'.

BRIEF DESCRIPTION OF THE PHOTOGRAPH

The accompanying photographs show as nearly true as it is reasonably possible to make the same, in a color illustration of this character, typical specimens of the plant parts of the new variety.

Figure 1:
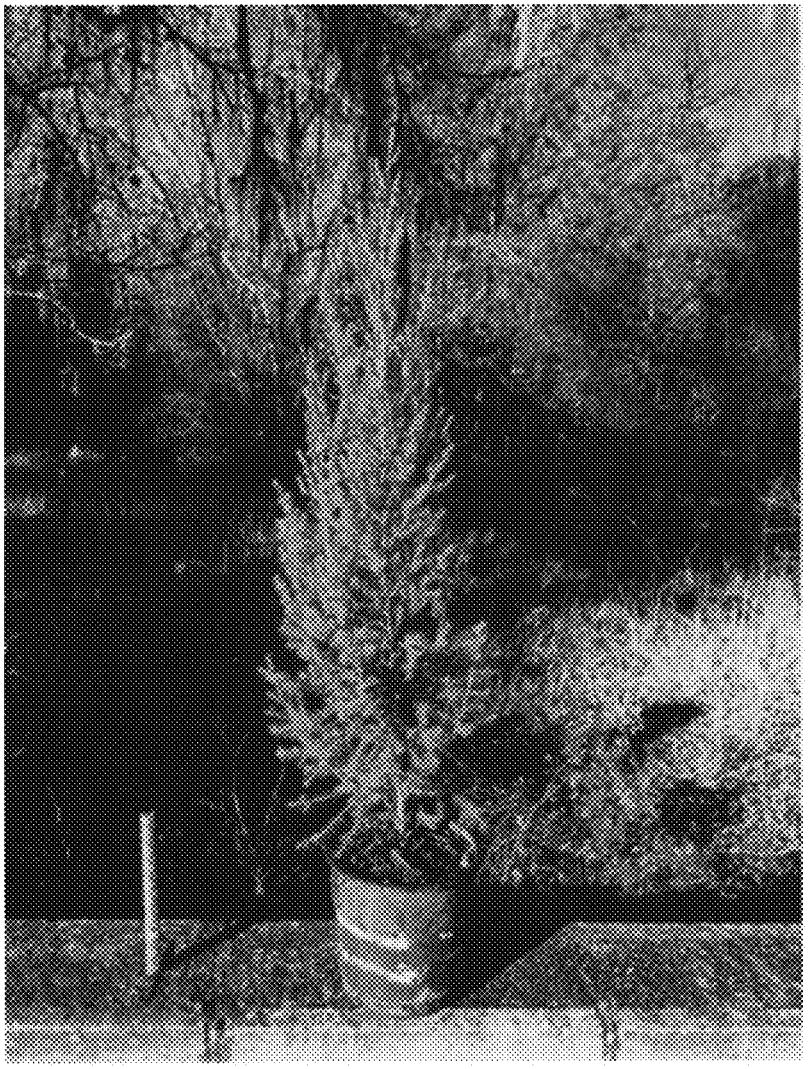

FIG. 1—illustrates a specimen of 4 months of age from the liner while growing outdoors in a pot.

Figure 2:
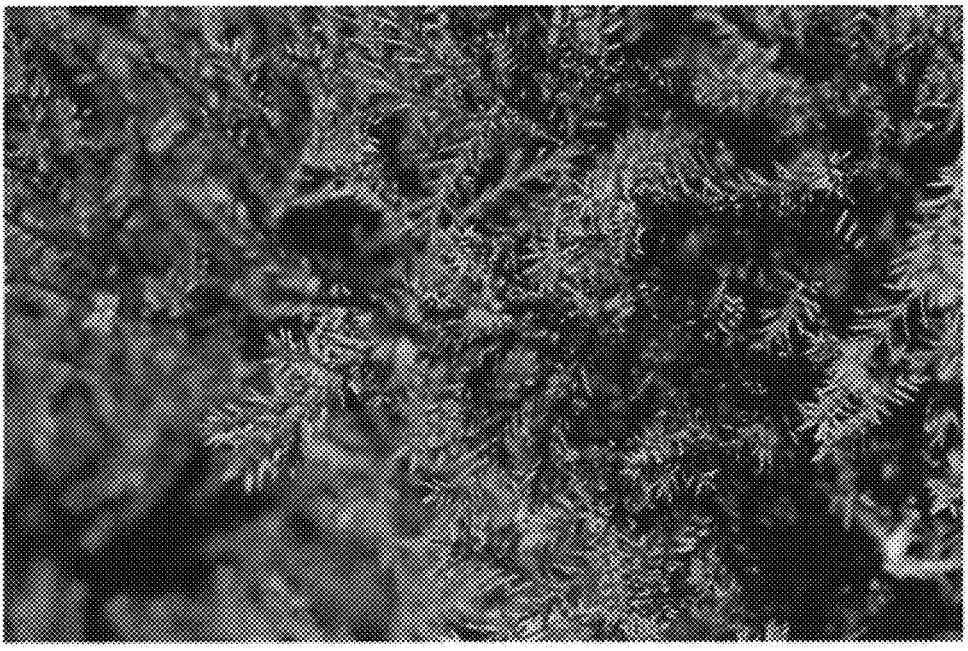

FIG. 2—illustrates a close-up view of the needles of the new variety of approximately 4.5 years of age growing outdoors in the ground at Brooksville, Fla.

Figure 3:
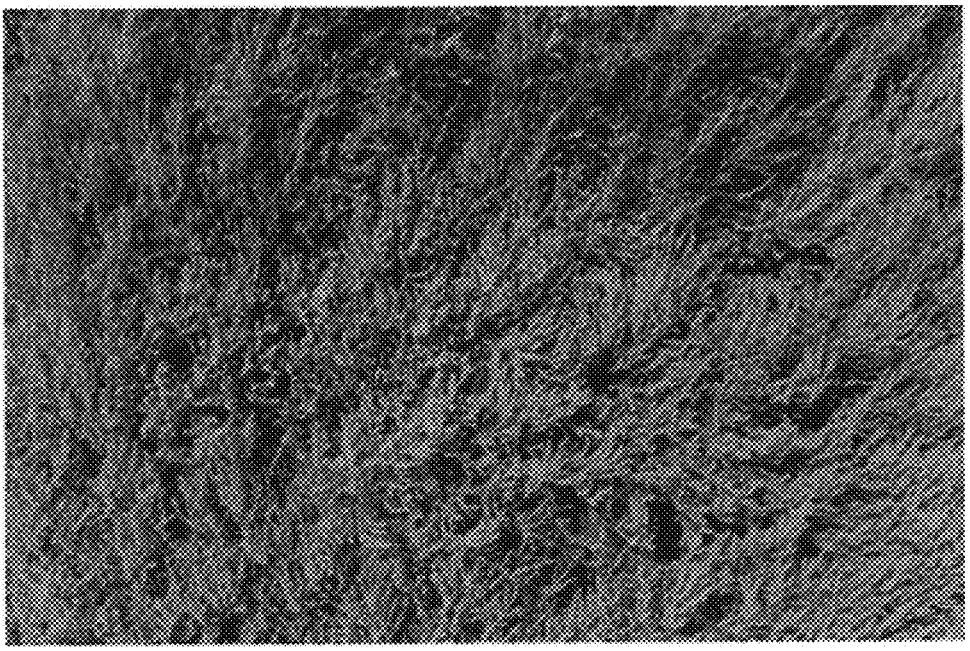

FIG. 3—illustrates a close-up view of the foliage of the new variety of approximately 4.5 years of age growing outdoors in the ground at Brooksville, Fla.

Figure 4:
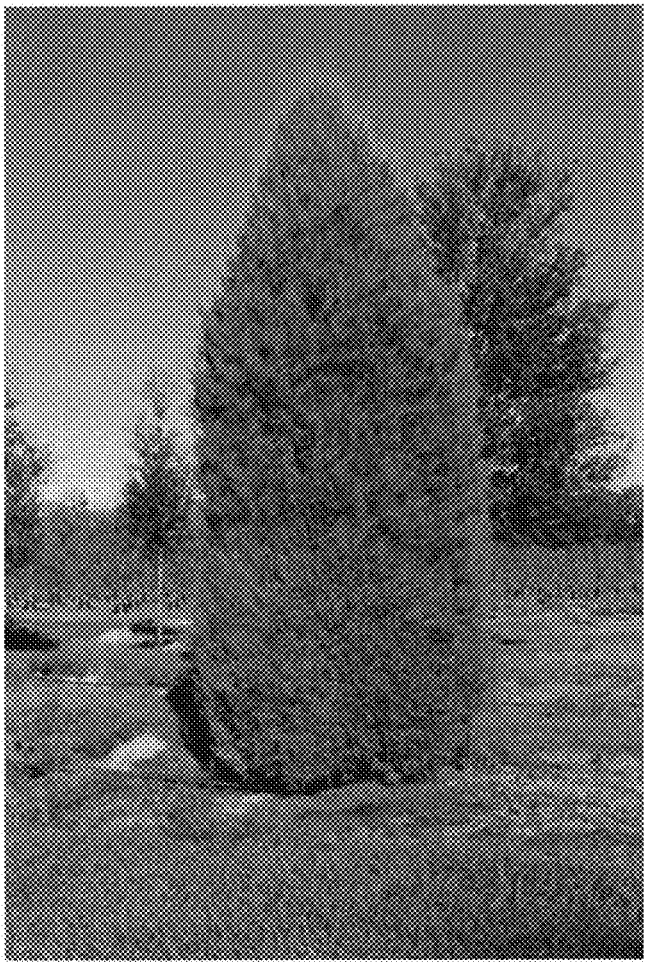

FIG. 4—illustrates specimen of approximately 4.5 years growing outdoors in the ground at Brooksville, Fla.

Figure 5:
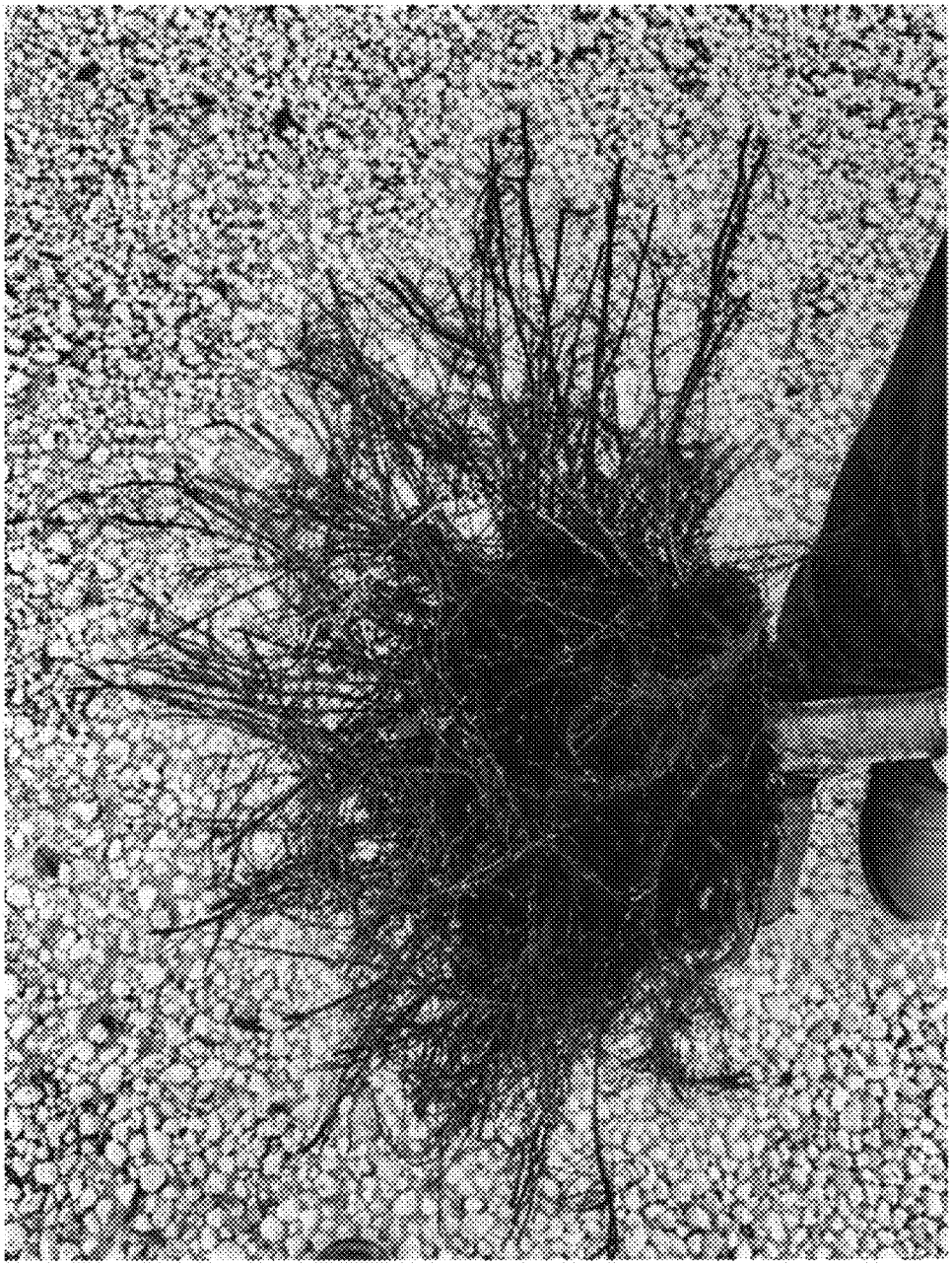

FIG. 5—illustrates the roots of the new variety, nine months after planting from a 3G Root Accelerator pot.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of 4.5-year-old specimens of the new variety during January 2019 while growing outdoors in the ground at Brooksville, Fla.

Class: Southern red cedar.

Plant:

*Form*.—Perennial evergreen tree.

*Height*.—Approximately 15 feet, on average.

*Width*.—Approximately 5.5 feet, on average.

*Tree shape*.—Pyramidal.

*Root habit*.—Fibrous, highly branching, and high density.

Trunk:

*Habit*.—Single central bole.

*Diameter near base*.—Approximately 5 inches at 12 inches above the ground.

*Bark*.—Texture: rough, peeling like. — color: commonly near Brown Group 200A.

Branches:

*Pattern*.—Alternating random.

*Density*.—Initially loose then becoming dense by the time the plant has reached approximately 4 feet in height.

*Stiffness*.—Medium.

*Branching angle*.—New branches: approximately 25 degrees. — mature branches: approximately 50 degrees.

*Color*.—Young branches: commonly near Brown Group 200D (same throughout all seasons). — mature branches: commonly near Brown Group 200C (same throughout all seasons).

*Size*.—Mature main branches: diameter at base is approximately ⅜ to ½ inches and length is approximately 42 inches, on average. — secondary branches: diameter at base is approximately ⅛ inches and length is approximately 13 inches on average.

*Branchlets*.—Size: approximately 4 inches in length on average. — attitude of the spray: semi-erect. — number per branch: many.

Needles:

*Shape*.—Acicular; apex is acute; base is flattened needle.

*Arrangement*.—Alternate.

*Size*.—Scale-like leaves: approximately 2 inches in length, ½ inches in width, and ⅛ inches in thickness, on average. — awl-shaped leaves: approximately 4 inches in length, ½ inches in width, and ¼ inches in thickness, on average.

*Texture*.—Upper and lower surfaces: needle like, prickly.

*Color*.—Young needle upper and under surfaces: commonly near Yellow-Green Group 143B. — mature needle upper and under surfaces: commonly near Yellow-Green Group 144A.

*Venation*.—Pattern and color none observed.

*Fragrance*.—Juniper-like.

Development:

*Hardiness*.—USDA Zone 8a-10a.

*Average growth per season*.—Approximately 4-5 feet in height, on average.

*Seed and pollen cones*.—Not yet produced or observed.

*Resistance to pests*.—Resistance to fungus, such as *Cercospora* Blight (*Cercospora angreci*), and spider mites, such as Southern Red Mite (*Oligonychus ilicis*).

The new 'CAN-SRC1' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Southern red cedar tree characterized by the following combination of characteristics:

(a) forms attractive, acicular shaped, alternate arranged needles (b) provides Juniper-like fragrance, (c) exhibits fibrous, highly branching, high density root habit, and (d) is well suited for providing attractive ornamentation; substantially as herein shown and described.

* * * * *